(12) United States Patent
Mukai

(10) Patent No.: US 6,168,278 B1
(45) Date of Patent: Jan. 2, 2001

(54) PROTECTIVE GOGGLES FOR LASER AND LASER TREATMENT APPARATUS WITH THE GOGGLES

(75) Inventor: Hideo Mukai, Toyohashi (JP)

(73) Assignee: Nidek Co., Ltd., Aichi (JP)

( * ) Notice: Under 35 U.S.C. 154(b), the term of this patent shall be extended for 0 days.

(21) Appl. No.: 09/471,418

(22) Filed: Dec. 23, 1999

(30) Foreign Application Priority Data

Dec. 24, 1998 (JP) .................................... 10-366328

(51) Int. Cl.$^7$ .................................................. G02B 21/00
(52) U.S. Cl. ...................... 359/612; 359/601; 359/608; 351/57; 351/158
(58) Field of Search ........................ 359/227–236, 359/601–615, 350–361; 351/44, 47, 57, 59, 158; 372/98–109; 2/431, 432, 426; 128/846, 857–858

(56) References Cited

U.S. PATENT DOCUMENTS

| | | | |
|---|---|---|---|
| 4,511,225 | * | 4/1985 | Lipson ..................................... 351/47 |
| 5,276,539 | * | 1/1994 | Humphrey .............................. 351/44 |
| 5,299,053 | * | 3/1994 | Kleinburg et al. .................... 359/227 |
| 5,349,392 | * | 9/1994 | Buffet ..................................... 351/57 |

FOREIGN PATENT DOCUMENTS 6-45677   2/1994   (JP) .

* cited by examiner

*Primary Examiner*—Thong Nguyen
(74) *Attorney, Agent, or Firm*—Finnegan, Henderson, Farabow, Garrett & Dunner, L.L.P.

(57) ABSTRACT

Protective goggles for protecting the eyes of an operator and others from a treatment laser beam emitted from a laser treatment apparatus is disclosed. The goggles include a protective filter which selectively blocks the treatment laser beam, an operating section for moving the filter in or from the front of the eyes of the operator who wears the goggles, and a control unit which controls the motions of the operating section in time for the emission of the laser beam from the laser apparatus.

19 Claims, 4 Drawing Sheets

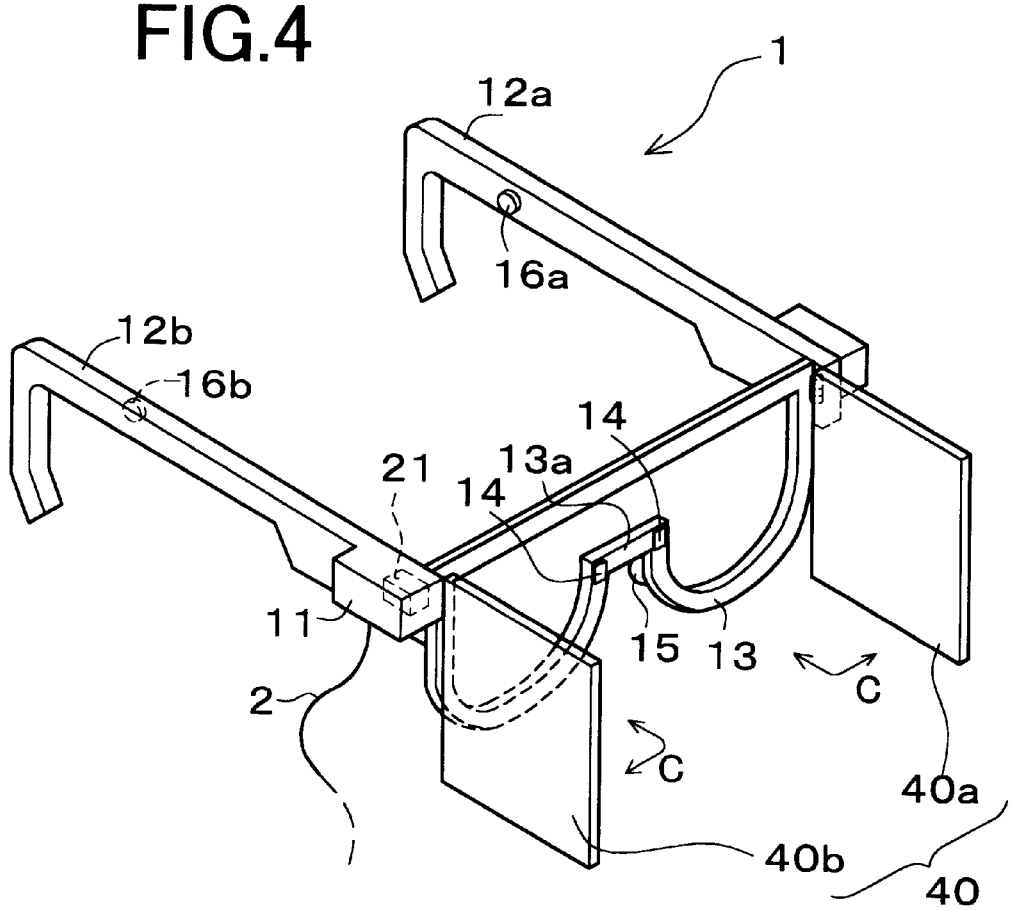

PROTECTIVE GOGGLES FOR LASER AND LASER TREATMENT APPARATUS WITH THE GOGGLES

BACKGROUND OF THE INVENTION

1. Field of the Invention

The present invention relates to protective goggles for laser, which is to be put on by a person for protecting his eyes from a laser beam, and also to a laser treatment apparatus with the goggles.

2. Description of Related Art

In a medical field, for example, when treatment is conducted on an affected part of a patient, which is an object to be irradiated with a treatment laser beam emitted from a laser treatment apparatus, an operator and his assistant(s) and others put on protective goggles for protecting the eyes from the treatment laser beam. Usually, this type of protective goggles is provided with a filter disposed in the front of part corresponding to the eyes of the operator, the filter having the property of blocking a wavelength of the treatment laser beam, but transmitting a visible light beam.

In plastic surgery and the like, a treatment laser beam having a wavelength in a visible region is generally used. The filter itself is therefore colored by coating or the like. The filter which blocks the visible treatment laser beam, however, would also reduce the transmittance of light having a wavelength near the wavelength of the treatment laser beam. As a result, the filter of the protective goggles prevents the operator who wears the goggles from looking clearly the condition of the affected part, as compared with the case in which the operator does not wear the goggles. If an aiming light has the wavelength near that of the treatment laser beam, the operator also could not clearly look the aiming light through the filter. In this case, accordingly, the operator or assistant has to put on the protective goggles prior to the irradiation of treatment laser beams, and take off the goggles every time to observe the affected part or perform aiming. Such the frequent putting-on or taking-off actions are very burdensome and may reduce operative efficiency. In particular, the operator generally uses both hands for holding a laser emitting element such as a hand piece and the like and retaining the position of the affected part. Handling of the protective goggles is then extremely troublesome.

SUMMARY OF THE INVENTION

The present invention has been made in view of the above circumstances and has an object to overcome the above problems and to provide protective goggles which are excellent in handling, needing no hands of a wearer (e.g., operator) who wears the goggles, and a laser treatment apparatus provided with the protective goggles.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided protective goggles to be put on by a wearer for protecting the eyes of the wearer from a laser beam emitted from a laser apparatus, the goggles including blocking means for selectively blocking the laser beam, insertion means for inserting or removing the blocking means in or from a front of the eyes of the wearer who wears the goggles, and control means for controlling motions of the insertion means in time for emission of the laser beam from the laser apparatus.

According to the second aspect of the present invention, there is provided a laser apparatus for irradiating an object with a laser beam, including a laser source which emits the laser beam, emission control means for controlling laser emission, protective goggles for laser to be put on by a wearer for protecting the eyes from the laser beam, and the protective goggles including, blocking means for selectively blocking the laser beam, and insertion means for inserting or removing the blocking means in or from the front of the eyes of the wearer who wears the goggles, insertion control means for controlling motions of the insertion means in time for emission of the laser beam.

According to the third aspect of the present invention, there is provided protective goggles for laser to be put on for protecting eyes of a wearer from a laser beam emitted from a laser apparatus, the goggles including a goggle frame having a support part to be securely supported on a head of the wearer, a filter attached to the goggle frame so as to be inserted or removed in or from the front of the eyes of the wearer for selectively blocking the laser beam, a filter moving mechanism provided in the goggle frame, and a control unit connected to the filter moving mechanism for controlling it based on a laser emission command signal.

According to the fourth aspect of the present invention, there is provided a laser apparatus for irradiating an object with a laser beam, including a main unit, a laser source disposed in the main unit, a laser emission control unit disposed in the main unit, protective goggles for laser to be put on by wearer for protecting eyes of the wearer from the laser beam, a filter provided in the protective goggles for selectively blocking the laser beam, a filter moving mechanism provided in the protective goggles, and a filter insertion control unit connected to the filter moving mechanism for controlling the filter moving mechanism based on a laser emission command signal.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 4 is another example of the protective goggles with a filter 40 having a different configuration from the embodiment.

DETAILED DESCRIPTION OF THE PREFERRED EMBODIMENTS

A detailed description of one preferred embodiment of protective goggles and a laser treatment apparatus with the goggles embodying the present invention will now be given referring to the accompanying drawings.

Figure 1:
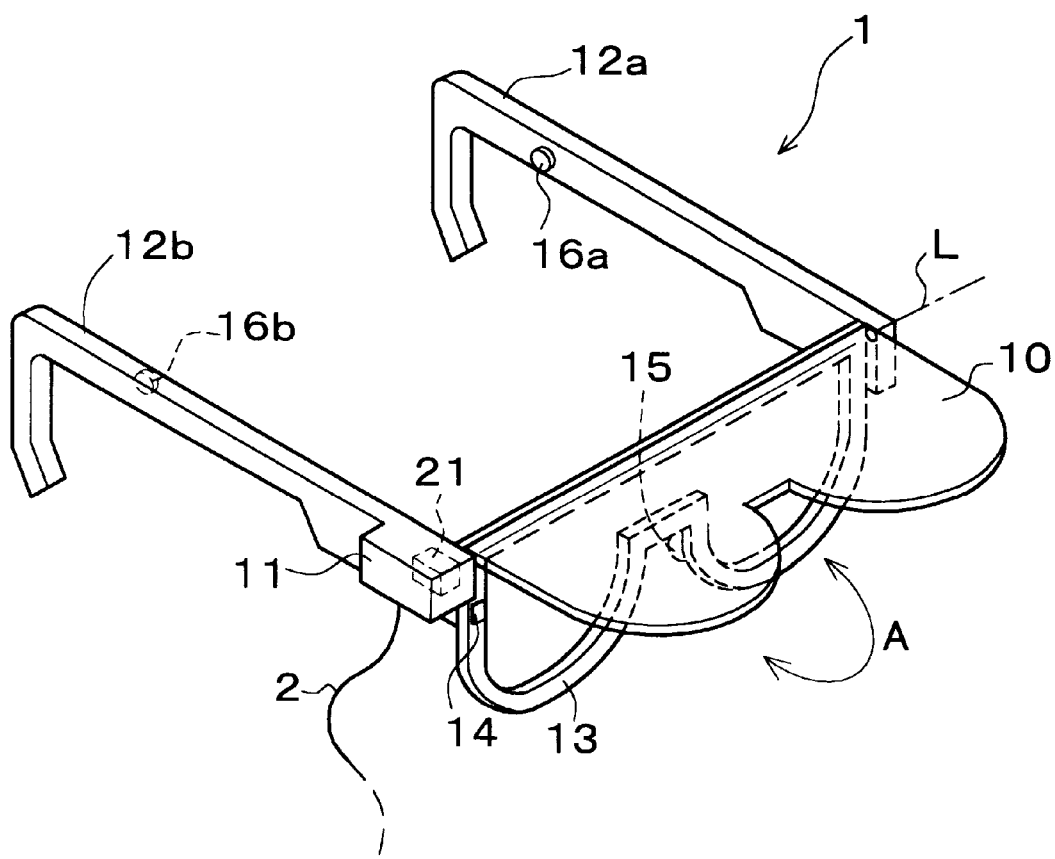
FIG. 1 is a schematic, perspective external view of protective goggles in an embodiment according to the present invention.
Figure 2:
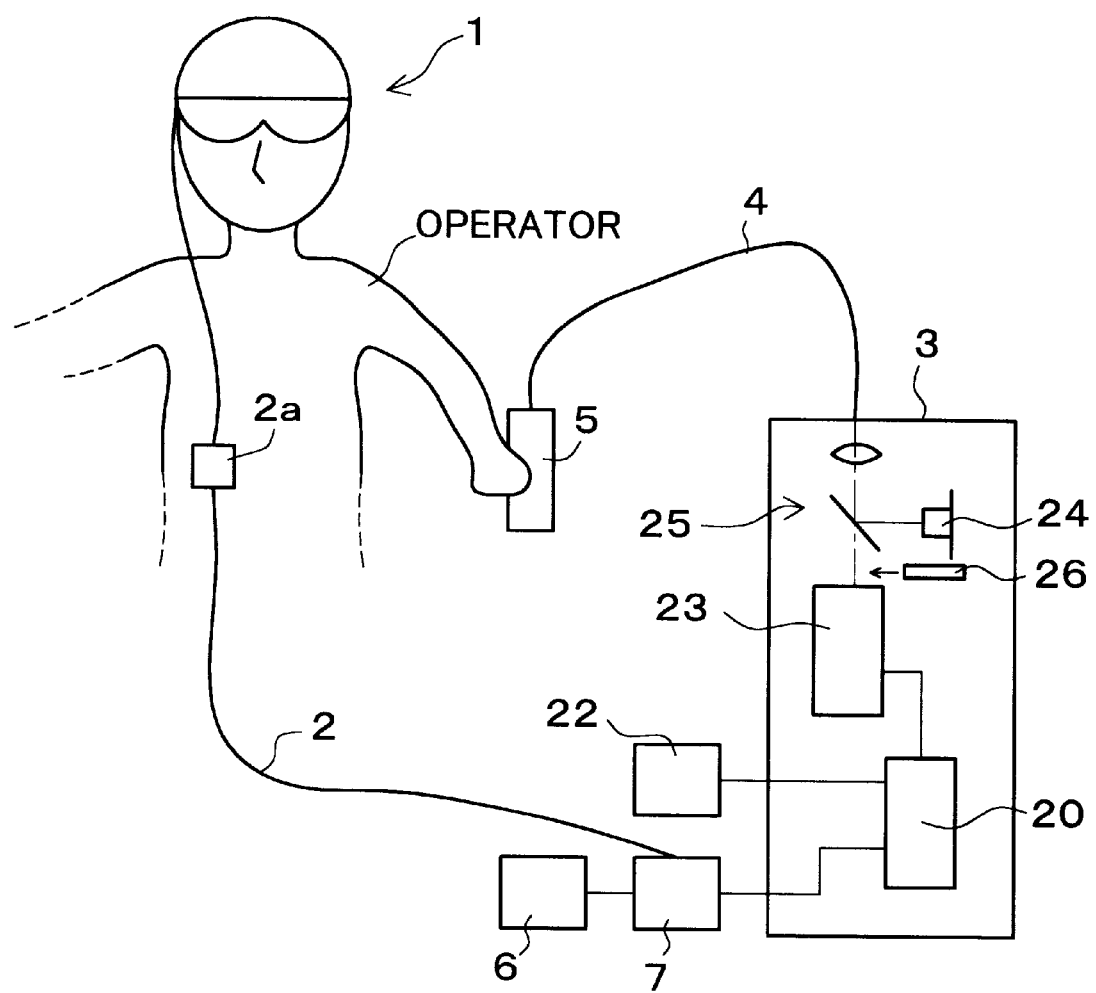
FIG. 2 is a schematic structural view of the protective goggles and a laser treatment apparatus in the embodiment according to the present invention.

FIG. 1 is a schematic, perspective external view of protective goggles in an embodiment according to the present invention. FIG. 2 is a schematic structural view of the whole laser treatment apparatus including the protective goggles. In the present embodiment, explanation is made on an example of a laser treatment apparatus for treatment of dermal hemangioma.

Reference numeral 1 denotes protective goggles, which is constructed in the form of a pair of spectacles mainly configured by a goggle frame 13 providing an opening in the front of the eyes of a wearer and earpieces 12a and 12b which serve as support parts to be supported on the head, or the ears of the wearer. Reference numeral 10 denotes a protective filter provided in the goggles 1. This filter 10 has the property of blocking a treatment laser beam (which is referred to as "treatment beam" hereinafter) having a wavelength of 532 nm, which is emitted from a main unit 3 of a laser treatment apparatus, while passing visible light beams excepting the treatment beam. The filter 10 is supported between the earpieces 12a and 12b extending from both sides of the frame 13, the filter 10 being rotatable about an axis L in a direction indicated by a double-headed arrow A. Reference numeral 11 is an operating section for actuating the filter 10 to open or close the space defined by the frame 13. The operating section 11 has internally a small-sized rotary solenoid 21. By actuation of this rotary solenoid 21, the filter 10 is moved to an open position or a closed position. At the open position, the filter 10 is placed at a substantial right angle with respect to the frame 13 as shown in FIG. 1. Accordingly, the filter 10 is out of the visual field, namely, the front of the eyes of a wearer (e.g., an operator), allowing the wearer to observe the affected part in a natural condition, not through the filter 10. To close the opening of the goggles, the rotary solenoid 21 is actuated to rotate the filter 10 so that it contacts with the frame 13. The filter 10 is thus inserted in the visual field of the wearer, so that the treatment beam can be prevented from entering the eyes of the wearer during emission of the treatment beam. Reference numeral 14 denotes a limit switch (sensor) for detecting the positional state, i.e., the opened and closed (insertion and removal) state of the filter 10. This limit switch 14 is disposed on the frame 13 so that the filter 10 comes into contact with the limit switch 14 when the filter 10 is moved to the closed position. Reference numeral 15 denotes a nose pad.

Limit switches (sensors) 16a and 16b are disposed in each inside of the earpieces 12a and 12b for detecting whether the goggles 1 have been put on by the wearer. The width between the earpieces 12a and 12b is slightly smaller than an average width of the head of the wearer so that the goggles 1 are securely fitted on the sides of the head of the wearer, when the switches 16a and 16b are thus turned on.

In FIG. 2, reference numeral 2 denotes a cable through which the rotary solenoid 21 receives a current for actuation and transmits/receives various signals to/from the main unit 3. Reference numeral 2a denotes a control box for the goggles 1. This control box 2a controls the actuation of the rotary solenoid 21 and the transmission/reception of signals as mentioned later.

In the main unit 3, there are disposed a laser source 23 which oscillates and emits a treatment beam for treating the affected part, a semiconductor laser source 24 which emits an aiming beam having a wavelength of 635 nm, an optical system 25 for introducing the laser beams to an optical fiber 4, and a control unit 20 which controls the actuation of the main unit 3. The laser source 23 used in the present embodiment is internally provided with a solid-state laser medium of an Nd:YAG rod which oscillates a fundamental wave with a wavelength of 1064 nm, a mirror for producing resonance, and nonlinear crystal, and others. The thus configured laser source 23 emits the treatment beam with a wavelength of 532 nm which is the second high harmonic wave. The optical fiber 4 is joined to the hand piece 5 from which the treatment beam and the aiming beam are emitted toward the affected part. Reference numeral 6 denotes a footswitch for inputting a trigger signal (i.e., a laser emission command signal) to start the emission of the treatment beam. The footswitch 6 and the control box 2a are individually linked to the control unit 20 via an interface 7.

The operation of the apparatus having the above configuration will be next explained. An operator connects the cable 2 to the interface 7 and puts on the goggles 1 to proceed a preparation of treatment. When the goggles 1 are put on by the operator, the limit switches 16a and 16b disposed on the insides of the earpieces 12a and 12b are turned on. These switch signals are transmitted to the control unit 20 through the control box 2a and the interface 7. The control unit 20, unless receives the signal representing that the goggles 1 have been put on by the operator, controls not to start emission of the treatment beam, for example, by maintaining a shutter 26 of the optical system 25 in the closed position or keeping the laser source 23 in a suspended state from working for laser emission.

After putting on the goggles 1, the operator operates switches on a control panel 22 connected to the control unit 20 to determine the irradiation conditions of the treatment beam to be emitted and the light quantity of the aiming beam, and aims the hand piece 5 at the affected part to appropriately project the aiming beam on the affected part, thereby proceeding to the preparation for irradiation of the treatment beam. At this time, the filter 10 is in the open position shown in FIG. 1, so that the goggles 1 provides a natural visual field for observation to the operator even while he wears the goggles 1. The operator can thus clearly observe the condition of the affected part and the aiming beam projected onto, and the operator can easily make preparations of treatment for the affected part, observations of the same, and so on, without difficulties.

Upon completion of alignment of the apparatus with respect to the affected part by observing the aiming beam, the operator presses the footswitch 6 to transmit an emission command signal for commanding emission of the treatment beam to the control unit 20 via the interface 7. The laser emission command signal from the footswitch 6 is also input in the control box 2a via the interface 7. On reception of the laser emission command signal, the control box 2a actuates the rotary solenoid 21 to rotate the filter 10 from the open position to the closed position. This makes it possible to place the filter 10 in the front of the eyes of the operator in preparation of laser irradiation, without using his hands.

When the limit switch 14 is depressed by the filter 10 when closed, a switch signal representing that the filter 10 has been closed is transmitted to the control box 2a. This signal is further transmitted to the control unit 20 via the interface 7. After the control unit 20 confirms that, in addition to the laser emission command signal from the footswitch 6, the signal representing the closing of the filter 10 has been input, the control unit 20 actuates the laser source 23 to emit the treatment beam and opens the shutter 26 to allow the treatment beam to pass. The treatment beam emitted from the laser source 23 passes through the optical fiber 4 and is output from the hand piece 5 toward the affected part.

When the operator stops pressing the footswitch 6, stopping the input of the laser emission command signal, the control unit 20 controls the laser source 23 to stop the emission of the treatment beam (alternatively, the control unit 20 actuates the shutter 26 to close). Simultaneously, the signal transmitted to the control box 2a via the interface 7 is discontinued. The control box 2a then actuates the rotary solenoid 21 to open the filter 10, specifically, by stopping supply of the current to the solenoid 21. With the filter 10 thus moved to the open position, the operator can easily and clearly observe the condition of the affected part after laser irradiation without needing any troublesome operations.

As mentioned above, the filter 10 is placed in the front of the eyes of the operator without using his hands in time for laser irradiation, and it is automatically removed from the front of the eyes upon the stop of the laser irradiation. Accordingly, without imposing manual works on the operator, i.e., putting-on and taking-off actions, the goggles 1 can ensure ease of observation of the affected part and others to the operator who wears the goggles 1. In particular, when the operator performs treatment by repeating laser irradiation and observation of the affected part after irradiation, he can be released from frequent works of putting on or taking off the goggles 1, thereby improving the efficiency of treatment. Even if the operator has to hold or retain the skin surface of the patient with one hand of the operator in order to facilitate the laser irradiation to the tissues of the affected part of the patient, the operator can also conduct treatment by using the hand piece 5 held with the other hand.

The present invention may be embodied in other specific forms without departing from the spirit or essential characteristics thereof. For instance, in the above-described embodiment, although the rotary solenoid 21 is used as a device for moving the filter 10 in or from the front of the eyes, it is not limited thereto. Instead of the rotary solenoid 21, a motor and the like may be used. Although the filter 10 in the embodiment is rotated about the axis L, it may be configured so as to slide up and down or right and left. Alternatively, the filter may be configured so as to open/close with hinged double plates.

Such the alternatives of the filter are illustrated in detail below.

Figure 3:
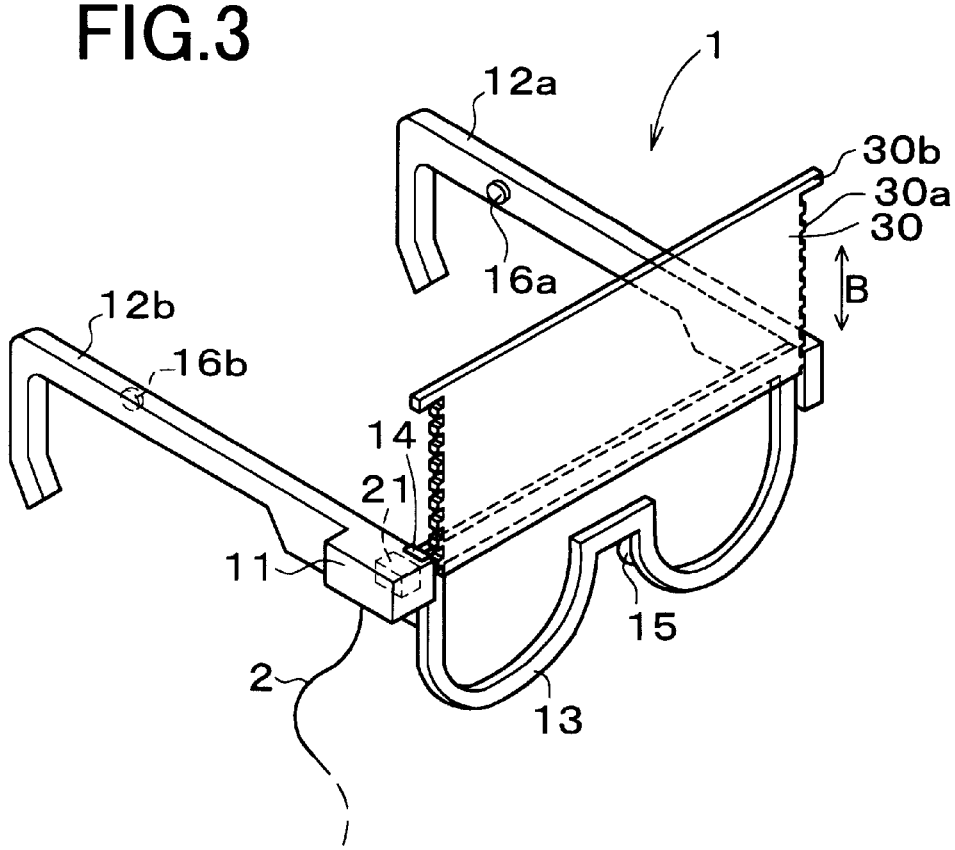
FIG. 3 is an example of the protective goggles with a filter 30 having a different configuration from the embodiment.

As a first alternative, FIG. 3 shows a filter 30 which is slid up and down. This filter 30 is provided with racks 30a which engage with pinions (not illustrated) provided in end portions of the earpieces 12a and 12b. As the pinions in the earpieces 12a and 12b are rotated, the filter 30 is slid up or down as indicated by a double-headed arrow B in FIG. 3 through the racks 30a. In this case, the limit switch 14 is disposed on each upper surface of the end portions of the earpieces 12a and 12b so that the switch 14 comes into contact with a sideways projection 30b of the filter 30 when closed (namely, slid down), thereby to detect the opened/closed state of the filter 30.

As a second example, FIG. 4 shows a filter 40 which is a double-doored type. This filter 40 is constructed of two plate-like filters 40a and 40b that are rotatably joined with the earpieces 12a and 12b respectively with hinges or the like connecting each side upper portion of the plates and the end portions of the earpieces 12a and 12b, so that the filters 40a and 40b are rotated as indicated by arrows C in FIG. 4. Specifically, the filters 40a and 40b are moved to open the opening of the frame 13 in time for the laser irradiation or close the same in time for the observation or the aiming with the aiming beam. In this case, the limit switches 14 are disposed on both sides of a bridge part 13a of the frame 13 so that the switches 14 come into contact with the filters 40a and 40b when closed, thereby to detect the opened/closed state of the filters 40a and 40b.

With the above configurations, as well as in the above embodiment, the filter(s) 30, 40 can be inserted in the visual field of the operator during the laser irradiation, but removed out of the visual field during the observation of the affected part of a patient or the aiming operation with the aiming beam.

Besides the above ways, various ways for inserting/removing the filter 10 in/from the visual field of the operator may be used.

The goggles 1 in the embodiment are connected to the main unit 3 through the cable 2. If using electromagnetic waves, on the other hand, the goggles 1 may be connected to the main unit 3 by wireless. This can be achieved by incorporating a system for signal transmission and reception into each of the main unit 3 and the goggles 1, e.g., the control box 2a or others.

The goggles 1 in the embodiment are in the form of a pair of spectacles having the nose pad 15 and the earpieces 12a and 12b which are support parts against the head of the wearer, but the goggles of the present invention may be applied to different types. For a person who wears spectacles, for example, the goggles may be constructed of a goggle frame capable of entirely covering the spectacles, a protective filter attached to the frame so that the filter is actuated to open or close in the same manner as in the above embodiment, and support parts such as belts and the like. The goggles 1 of this type is put on by the wearer with spectacles on by fastening the support parts of the goggles 1 to each other at the back of the head.

Furthermore, although the laser treatment apparatus in the above embodiment emits a treatment beam having a single wavelength, the laser treatment apparatus may be configured so as to emit treatment beams having plural wavelengths. In this case, if a pair of protective goggles is used for preventing the transmittance of all the wavelengths of laser beams, the protective filter of the goggles has to be inevitably, more deeply colored. Such the filter makes it further difficult for the wearer (the operator) who wears the goggles to confirm or observe the aiming beam and the affected part. Consequently, the protective goggles of the present invention are more effective when it is applied to such the case of using plural wavelengths.

The protective filter may be configured so as to be exchangeable. If plural protective filters which block different wavelengths are prepared for exchange, a pair of goggles can be used for laser beams of different wavelengths.

According to the above embodiment of the present invention, the protective filter can be appropriately inserted in or removed from the front of the eyes (i.e., the visual field) of the wearer according to each timing of laser irradiation, observation of the affected part or projection of the aiming beam, without needing the actions of the wearer to put on or take off the goggles 1.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. Protective goggles to be put on by a wearer for protecting the eyes of the wearer from a laser beam emitted from a laser apparatus, the goggles including:

blocking means for selectively blocking the laser beam;

insertion means for inserting or removing the blocking means in or from a front of the eyes of the wearer who wears the goggles; and control means for controlling motions of the insertion means in time for emission of the laser beam from the laser apparatus.

2. The protective goggles according to claim 1 further including first detection means for detecting whether the protective goggles have been put on by the wearer.

3. The protective goggles according to claim 1 further including second detection means for detecting whether the blocking means has been inserted in the front of the eyes of the wearer.

4. The protective goggles according to claim 1, wherein the blocking means includes a filter for selectively blocking the laser beam according to wavelengths.

5. The protective goggles according to claim 1, wherein the blocking means is removably attached to the protective goggles.

6. A laser apparatus for irradiating an object with a laser beam, including:

a laser source which emits the laser beam;

emission control means for controlling laser emission;

protective goggles for laser to be put on by a wearer for protecting the eyes from the laser beam; and the protective goggles including, blocking means for selectively blocking the laser beam, and insertion means for inserting or removing the blocking means in or from the front of the eyes of the wearer who wears the goggles, insertion control means for controlling motions of the insertion means in time for emission of the laser beam.

7. The laser apparatus according to claim 6 further including input means for inputting a laser emission command signal, the insertion control means controlling motions of the insertion means based on the laser emission command signal.

8. The laser apparatus according to claim 6, wherein the protective goggles includes first detection means for detecting whether the protective goggles have been put on by the wearer, and the emission control means controls the laser emission based on detection results of the first detection means.

9. The laser apparatus according to claim 6, wherein the protective goggles includes second detection means for detecting whether the blocking means has been inserted in the front of eyes of the wearer, and the emission control means controls the laser emission based on detection results of the second detection means.

10. Protective goggles for laser to be put on for protecting eyes of a wearer from a laser beam emitted from a laser apparatus, the goggles including:

a goggle frame having a support part to be securely supported on a head of the wearer;

a filter attached to the goggle frame so as to be inserted or removed in or from the front of the eyes of the wearer for selectively blocking the laser beam;

a filter moving mechanism provided in the goggle frame; and a control unit connected to the filter moving mechanism for controlling it based on a laser emission command signal.

11. The protective goggles according to claim 10 further including a first sensor provided in the goggle frame for detecting whether the protective goggles have been put on by the wearer, this sensor being disposed so as to be contactable with the wearer when the protective goggles are put on by the wearer.

12. The protective goggles according to claim 10 further including a second sensor provided in the goggle frame for detecting whether the filter has been inserted in the front of the eyes of the wearer.

13. The protective goggles according to claim 10, wherein the filter includes a wavelength selection filter for selectively blocking the laser beam according to wavelengths.

14. The protective goggles according to claim 10, wherein the filter is removably attached to the goggle frame.

15. The protective goggles according to claim 10 wherein the filter moving mechanism rotates the filter about a predetermined axis of the goggle frame.

16. A laser apparatus for irradiating an object with a laser beam, including:

a main unit;

a laser source disposed in the main unit;

a laser emission control unit disposed in the main unit;

protective goggles for laser to be put on by wearer for protecting eyes of the wearer from the laser beam;

a filter provided in the protective goggles for selectively blocking the laser beam;

a filter moving mechanism provided in the protective goggles; and a filter insertion control unit connected to the filter moving mechanism for controlling the filter moving mechanism based on a laser emission command signal.

17. The laser apparatus according to claim 16 further including a trigger switch connected to the laser emission control unit and the filter insertion control unit, for inputting the laser emission command signal.

18. The laser apparatus according to claim 16 further including a first sensor for detecting a putting condition of the protective goggles, the sensor being provided in the protective goggles and connected to the laser emission control unit.

19. The laser apparatus according to claim 16 further including a second sensor for detecting an inserting/removing condition of the filter, the sensor being provided in the protective goggles and connected to the laser emission control unit.

* * * * *